United States Patent [19]

Mauck et al.

[11] Patent Number: 5,075,221
[45] Date of Patent: Dec. 24, 1991

[54] STABILIZED EXTRACTION COMPOSITION CONTAINING A SULFHYDRYL-CONTAINING REDUCING AGENT AND ITS USE IN CHLAMYDIAL AND GONOCOCCAL DETERMINATIONS

[75] Inventors: John C. Mauck; Robert W. Zercie, both of Rochester, N.Y.

[73] Assignee: Eastman Kodak Company, Rochester, N.Y.

[21] Appl. No.: 255,921

[22] Filed: Oct. 7, 1988

[51] Int. Cl.[5] .................. C12Q 1/00; G01N 33/53
[52] U.S. Cl. .................. 435/7.36; 436/176; 436/826
[58] Field of Search .............. 435/188, 7, 803, 814, 435/820, 259, 7.36; 530/364, 403, 412, 421, 422, 424; 436/511, 174, 176, 825, 826, 510

[56] References Cited

U.S. PATENT DOCUMENTS

| | | | |
|---|---|---|---|
| 3,860,484 | 1/1975 | O'Malley | 435/188 |
| 4,150,950 | 4/1979 | Takeguchi et al. | |
| 4,339,533 | 7/1982 | Chu | |
| 4,427,782 | 1/1984 | Caldwell et al. | |
| 4,497,899 | 2/1985 | Armstrong et al. | |
| 4,497,900 | 2/1985 | Abram et al. | 436/511 |
| 4,540,565 | 9/1985 | Roman, Jr. et al. | |
| 4,828,978 | 5/1989 | Warren et al. | 436/511 |
| 4,830,960 | 5/1989 | Appleton | 436/518 |
| 4,874,691 | 10/1989 | Chandler | 436/535 |

FOREIGN PATENT DOCUMENTS

| | | |
|---|---|---|
| 0193431 | 9/1986 | European Pat. Off. . |
| 0252750 | 1/1988 | European Pat. Off. . |
| 0264036 | 4/1988 | European Pat. Off. . |
| 182804 | 3/1984 | Japan . |

OTHER PUBLICATIONS

Schnaar et al.-Analytical Biochemistry vol. 151 (1985) pp. 268-281.
Toray-Chem. Abst. vol. 102(1985) p. 94214x.
Schnaar et al.-Chem. Abst. vol. 104(1986) p. 48244a.
Caldwell et al., *Infect & Immun.*, 44 (2), pp. 306-314 (1984).
Newhall et al., *J. Bact.*, 154 (2), pp. 998-1001 (1983).
U.S. Ser. No. 136,166, filed 12/18/87, by McClune et al.

*Primary Examiner*—Sam Rosen
*Attorney, Agent, or Firm*—J. Lanny Tucker

[57] ABSTRACT

A composition including a sulfhydryl-containing reducing agent is stabilized for long term storage with a hydrophilic polymer. This composition can be combined with one or more reagents useful for extracting antigens from chlamydial or gonococcal organisms. The extracted antigen can be determined using immunological reactions and appropriate labeled reactants.

16 Claims, No Drawings

STABILIZED EXTRACTION COMPOSITION CONTAINING A SULFHYDRYL-CONTAINING REDUCING AGENT AND ITS USE IN CHLAMYDIAL AND GONOCOCCAL DETERMINATIONS

FIELD OF THE INVENTION

The present invention relates to a composition comprising a stabilized sulfhydryl-containing reducing agent, to an extraction composition and to its use for extraction of antigen from chlamydial or gonococcal organism for diagnostic determinations.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is Chlamydia trachomatis (herein C. trachomatis) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from C. trachomatis is pervasive in the general population so that it is believed that there are millions of cases each year of nongonococcal urethritis alone.

Gonorrhea is a disease usually transmitted by sexual contact caused by a bacterium of the Neisseria genus, especially N. gonorrhoeae. The disease has plagued mankind for thousands of years, and although antibiotics have helped control its spread, it still persists in epidemic proportions in many parts of the world. The importance of detection and treatment of this organism is well recognized. N. meningitidis and N. lactamica are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract detectable antigen from chlamydial organisms. See for example, U.S. Pat. No. 4,427,782 (issued Jan. 24, 1984 to Caldwell et al) and E.P. Publication 193,431 (Caldwell et al).

Assays for C. trachomatis and N. gonorrhoeae carried out using a solid support are described in U.S. Pat. No. 4,497,899 and 4,497,900, respectively (both issued Feb. 5, 1985 to Armstrong et al and Abram et al, respectively). Extraction is carried out using various nonionic or anionic surfactants. In addition, the '899 patent mentions that it is preferred to include a reducing agent (such as dithiothreitol, 2-mercaptoethanol or N-acetylcysteine) in the chlamydial extraction medium.

Dithiothreitol is used in the extraction procedures described in U.S. Pat. No. 4,427,782 and E.P. Publication 193,431 (both noted above).

While dithiothreitol or other sulfhydryl-containing reducing agents are known to be useful in chlamydial antigen extraction to solubilize extraneous proteins, such agents are generally unstable, and rapidly lose their activity unless used right away. Therefore, it would be desirable to have extraction compositions and diagnostic test kits which can be stored for a lengthy period of time. Without this stability, such materials lack significant commercial interest.

SUMMARY OF THE INVENTION

The problems noted above with known extraction compositions and analytical methods are overcome with a composition comprising a sulfhydryl-containing reducing agent, and one or more hydrophilic polymers.

Moreover, this invention also provides an article comprising a water-insoluble substrate having thereon a dried coating of the composition noted above.

In addition, an extraction composition useful for the extraction of chlamydial or gonococcal antigen from chlamydial or gonococcal organisms, respectively, comprises one or more reagents useful for extracting chlamydial or gonococcal antigen, a sulfhydryl-containing reducing agent, and one or more hydrophilic polymers.

A diagnostic test kit useful for the determination of chlamydial or gonococcal antigens comprises:

(a) an extraction solution comprising one or more reagents useful for extraction chlamydial or gonococcal antigen from chlamydial or gonococcal organisms, respectively, and (b) an aqueous composition comprising a sulfhydryl-containing reducing agent, and one or more hydrophilic polymers.

Alternatively, a test kit can include the extraction solution with the article having a dried coating described above in place of an aqueous composition.

This invention also includes a method for extracting antigen from chlamydial or gonococcal organisms comprising:

A. providing a specimen suspected of containing chlamydial or gonococcal organisms, and B. extracting chlamydial or gonococcal antigen from the organisms, respectively, by contacting the specimen with the extraction composition described above.

Moreover, a method for the determination of a chlamydial or gonococcal antigen comprises:

A. extracting chlamydial or gonococcal antigen from a specimen suspected of containing chlamydial or gonococcal organisms, respectively, with the extraction composition described above, B. contacting the extracted antigen with antibodies thereto to form an immunological complex, and C. determining the presence of the complex as an indication of the presence of chlamydial or gonococcal organisms, respectively, in the specimen.

The extraction composition of this invention rapidly and effectively lyses chlamydial or gonococcal organisms in a biological specimen to release sufficient antigen for a sensitive assay. Lysis can be carried out very quickly, usually in a matter of a few minutes, and at room temperature using simple equipment and procedures. Both the lipopolysaccharide and major outer membrane protein chlamydial antigens are extracted, although the lipopolysaccharide antigen is of particular interest.

While it is known to use dithiothreitol or other sulfhydryl-containing reducing agents in extracting such antigens, the present invention provides a significant advance in the art by stabilizing the reducing agent so it can be stored for an extended period of time. This enables the assay to be performed weeks or months after diagnostic kit components are manufactured. Thus, the assay and kit have substantial commercial value unlike those taught in the art.

The advantages just noted are achieved by using the reducing agent in admixture with a hydrophilic polymer (defined below).

DETAILED DESCRIPTION OF THE INVENTION

The present invention includes an extraction method, as well as a method for determining the presence of chlamydial or gonococcal organisms in a biological specimen which has been obtained from a patient using standard medical and microbiological techniques. Such specimens include, for example, swab specimens obtained from the cervix, urethra, eyes, throat or anus of a patient, and body fluids such as synovial fluid or fluid from lesions. The biological specimens so obtained are suspected of containing chlamydial or gonococcal bacterial organisms which comprise the antigens to be determined.

While some assays in the art are designed to detect whole bacterial cells, it is an advantage of this invention that the cells are effectively lysed and sufficient antigen extracted from the cellular matter to provide a sensitive assay in a relatively short period of time.

The chlamydial antigens generally detected according to the present invention are the lipopolysaccharide (glycolipid group) antigen of the organism as described, for example, in E.P. Publication 193,431 (noted above), and the major outer membrane protein of the organism as described in U.S. Pat. No. 4,427,782 (noted above). In one embodiment, both antigens are detected simultaneously. However, the lipopolysaccharide antigen is of most interest in the practice of a preferred embodiment to detect *C. trachomatis*.

In other embodiments, various gonococcal organisms, such as *N. gonorrhoeae*, are detected by determining the presence of extracted major outer membrane proteins IA and IB antigens from the organisms. A single strain may be detected, but preferably, a mixture of strains is detected.

The critical feature of the present invention is the use of a sulfhydryl-containing reducing agent in the extraction procedure in combination with one or more hydrophilic polymeric binder materials which provide stability for the reducing agent.

The reducing agents useful in this invention are capable of breaking disulfide bonds in proteins, peptides or components thereof. Examples of useful reducing agents include, but are not limited to, thiols such as 1,3-dimercapto-2-propanol, 2,3-dimercapto-1-propanol, 1,2-dimercaptoethane, dithiothreitol, dithioerythritol, mercaptoethanol and thioglycerol. Other useful compounds are glutathione, N-actylcysteine, cysteine, thioglycolic acid, L-cysteinemethyl ester, L-cysteineethyl ester and N-acetyl-D,L-isocysteine. The thiols are preferred with dithiothreitol being most preferred in the practice of this invention. These reducing agents are generally available from commercial sources.

The reducing agent is used in admixture with one or more hydrophilic polymers. Such polymers are considered water-soluble or water-dispersible and include vinylpyrrolidone polymers, acrylamide and methacrylamide polymers, acrylic and methacrylic acid polymers, polyethylene glycols and polyamines. Both homo- and copolymers are useful as long as the component repeating units making up the copolymers are such as to provide the desired hydrophilicity.

Representative polymers include, but are not limited to: poly(acrylic acid), poly(methacrylic acid), poly(acrylic acid-co-methyl acrylate) (90:10 weight ratio), poly(acrylamide), poly(acrylamide-co-acrylic acid) (50:50 weight ratio), poly(methacrylamide-co-methacrylic acid) (70:30 weight ratio), polyamines such as those described in U.S. Pat. Nos. 3,702,249, and 4,689,359, and polyethylene glycols. Also useful are vinylpyrrolidone homo- and copolymers such as poly(vinylpyrrolidone), poly(vinylpyrrolidone-co-acrylic acid) (60:40 weight ratio), poly(vinylpyrrolidone-co-acrylamide) (50:50 weight ratio) and poly(vinylpyrrolidone-co-methacrylamide-co-acrylic acid) (75:10:15 weight ratio). Preferred polymers are vinylpyrrolidone polymers, acrylamide polymers (including methacrylamide polymers) and copolymers of vinyl pyrrolidone and acrylamide monomers. A most preferred polymer in the practice of this invention is poly(acrylamide).

These polymers are generally prepared using standard emulsion polymerization techniques, and can be used in suspension as latex particles, or they can be dried in admixture with the reducing agent to form a polymeric film. Many of the polymers can be obtained commercially.

In the practice of this invention, the reducing agent and hydrophilic polymer are generally used together in a weight ratio of at least about 1:10 of polymer to reducing agent. Preferably, this ratio is from about 1:5 to about 5:1. In an aqueous composition of polymer and reducing agent, the reducing agent is generally present in an amount of at least about 5 mmolar, with from about 20 to about 50 mmolar being preferred.

The reducing agent and the hydrophilic polymer can be supplied in an aqueous composition generally containing one or more suitable buffers. Generally, this composition is buffered for a pH of from about 5 to about 7. It is useful in the process of extracting antigen from chlamydial or gonococcal organisms. This composition can be used alone in a separate step of the extraction process, or can be included as part of an extraction composition further comprising one or more extraction reagents.

In a preferred embodiment, the reducing agent and hydrophilic polymer are coated in admixture onto a water-insoluble substrate and dried for use at a later time. For example, this mixture can be coated on an article such as a polymeric film, glass slide or on the inside wall of a test tube, extraction device or other substrate readily determined by one skilled in the art. Useful substrates can be prepared from polymeric films, cellulosic materials, glass, ceramics, metals, and other materials readily determined by one skilled in the art. It is particularly preferred that the mixture be coated on the inside of an extraction device or tube into which other extraction reagents can be added to solubilize the dried materials and to extract antigen. Representative extraction devices are shown in U.S. Pat. No. 4,746,614 (issued May 24, 1988 to Devaney, Jr. et al).

It is particularly useful in the practice of this invention to use an extraction device as described above having the dried coating of reducing agent and polymer situated in one location on the substrate, and dried coatings of one or more other reagents (such as buffers or extraction reagents) situated in other separate locations on the substrate. Preferably, such a second reagent is a buffer such as mentioned herein.

Extraction of antigen can be accomplished using any standard extraction composition including one or more reagents useful for extracting chlamydial or gonococcal antigens, such as surfactants, enzymes, bile salts and others known in the art. There is considerable literature which describes such extraction reagents.

In a preferred embodiment, extraction is carried out using the extraction composition described and claimed in copending U.S. Ser. No. 255,928 filed on even date herewith by Pronovost, Mauck, Sullivan, Greer and Gilbert and entitled "High pH Extraction Composition and Its Use to Determine a Chlamydial, Gonococcal or Herpes Antigen".

This preferred extraction composition has a pH of at least about 8, and preferably at least about 9. A pH of at least 10 is most preferred. Generally, the appropriate pH is provided by including appropriate amounts of a buffer or strong base in the composition. As used herein, the term "strong base" is intended to mean a compound which has a pKa of at least about 8 at 25° C. Preferred strong bases have a pKa of at least about 9 at 25° C. Useful bases would be readily apparent to one skilled in the art, and include alkali metal, alkaline earth and ammonium hydroxides (such as sodium hydroxide, potassium hydroxide, calcium hydroxide, ammonium hydroxide and lithium hydroxide), phosphates (such as trisodium phosphate, and tripotassium phosphate), tri(hydroxymethyl)aminomethane and similar compounds. The amount of strong base in the composition would vary depending upon the pKa of the base, but generally from about 1 to about 30 mg/ml is useful, and from about 2 to about 20 mg/ml is preferred.

The extraction composition can further comprise, if desired, an alcoholamine in an amount of from about 1, and preferably from about 2 to about 30, mg/ml. Useful alcoholamines include ethanolamine, diethanolamine, propanolamine, triethanolamine and salts thereof. Others would be readily apparent to one skilled in the art.

Other addenda are preferably included in the extraction composition, including a cationic surfactant (especially when extraction of the major outer membrane protein is desired), preservatives to prevent hydrogen peroxide activity, chelating agents and anti-foaming agents.

Preferably, the extraction composition contains a sulfhydryl-containing reducing agent as described above in an amount of at least about 5, and preferably from about 20 to about 50, mmolar. Likewise, the preferred extraction composition also contains one or more hydrophilic polymers as described above in the appropriate amount.

When the test specimen contains whole blood or mucous, the extraction composition of this invention is desirably used with one or more proteases (described below) to break down blood or mucous components so they will not interfere with the assay. Proteases are a group of enzymes which hydrolyze the peptide bonds of proteins and form smaller polypeptides. They can be obtained from various sources, including microorganisms, such as bacteria and fungi, animal or human organs (for example the pancreas) plants (such as papaya) and others known in the art. Proteases can also be obtained from genetically altered microorganisms. Many proteases are commercially available (for example from Sigma Chemical Co.). Further details about useful proteases are provided in copending U.S. Ser. No. 255,922 filed on even date herewith by Gilbert, Mauck and Stowers and entitled "Use of a Protease in the Extraction of Chlamydial, Gonococcal and Herpes Antigens", incorporated herein by reference.

When a protease is used in an extraction process, the specimen can be contacted therewith either prior to or after contact with the extraction composition of this invention, but preferably prior to such contact.

Extraction can be carried out by providing a biological specimen suspected of containing chlamydial or gonococcal organisms and contacting (that is, incubating) it with the extraction composition of this invention in a suitable container for enough time to lyse the cells and extract antigen for assay. Generally, the extraction procedure takes less than 10 minutes although a longer time may be desired with certain specimens. Contact is generally carried out at room temperature (that is, from 18° to 25° C.), but higher temperature up to about 40° C. may be used if desired. However, the higher temperatures required in the art can be avoided by practicing this invention. Agitation of the specimen may be desirable. Extraction can be carried out in any suitable container. Preferably, it is carried out in a suitable extraction device which may be designed specially for that purpose. A number of such devices are known in the art, such as U.S. Pat. No. 4,746,614 (noted above).

After suitable incubation, the solution containing extracted antigen can be neutralized with a suitable acid to reduce the pH to between 6 and 8, if desired. It may also be treated to remove endogenous peroxides. Once the antigen is extracted from the organisms, it is desirable, although not essential, that the noted solution be prefiltered to remove cellular debris, particulate matter and other unwanted materials prior to further handling. Prefiltering can be carried out in a suitable container having a filter of some type.

The filtered specimen is then subjected to any of a number of analytical procedures in order to determine the presence of extracted antigen. Such procedures include culture techniques, counterimmunoelectrophoresis and serological tests which, while not preferred, may be the only choice in certain instances.

Preferably, the extracted antigen is detected using an immunoassay in which it is immunologically reacted with one or more appropriate antibodies. The resulting immunological complex is detected using a suitable radiometric, colorimetric, fluorometric or enzyme labeled reagent. In some cases, the reagent is a labeled antibody to the antigen, and in other cases, the labeled anti-antibody is directed to an unlabeled antibody which is reactive with the antigen. Such immunoassays generally include the formation of a detectable immunological complex on a solid support of some type, either coated or uncoated, followed by appropriate detection procedures. Other assays involve agglutination of the immunological complex when at least one reactant of the complex is attached to labeled or unlabeled particles of some type that clump together during complex formation.

Examples of useful assays include competitive immunoassays or enzyme-linked immunoabsorbent assays (or what is commonly called "ELISA"). Such assays are described generally in U.S. Pat. No. 4,427,782 (noted above) and by Schmeer et al, *J. Clin. Microbiol.*, 15(5), pp. 830-834 (1982). The chlamydial or gonococcal antibodies used can be directed to either or several antigens being extracted from the organisms. In one embodiment, antibodies are directed to a single antigen, such as the lipopolysaccharide of the *C. trachomatis*. In other embodiments, a mixture of different antibodies is directed to several antigens, such as those extracted from several gonococcal strains.

A similar solid phase immunoassay is described in U.S. Pat. Nos. 4,497,899 and 4,497,900 (both noted above) in which extracted antigen is adsorbed to an uncoated support by incubation at elevated temperatures over a lengthy time.

A preferred immunoassay is described and claimed in copending and commonly assigned U.S. Ser. No. 255,923 filed on even date herewith by Pronovost and entitled "Determination of a Chlamydial or Gonococcal Antigen Using A Positively-Charged Ionically Binding Support". Generally, this assay is described as follows. Further details can be obtained by consulting the noted application. The extracted antigen is contacted with a polymeric solid support which has a multiplicity of positively charged groups on the surface thereof. This support can be constructed of any natural or synthetic polymeric material with suitable cationic groups thereon which will ionically bind to the extracted antigen. Useful polymers include polyesters, polyamide, polycarbonates, polyethyleneimines, cellulosic materials, addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary primidinium salts or quaternary imidazolium salts, with quaternary ammonium salts being preferred.

The polymeric support (coated or uncoated) can be configured in any suitable form, such as beads, films, gels or membranes. A microporous membrane is preferred. Membranes (charged or uncharged) coated with surfactants are also useful.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 98,248 (filed Sept. 18, 1987 by Hinckley).

Almost immediately upon contact of the antigen with the charged support, the antigen is bound preferentially directly to the support. By "directly" is meant that the antigen is not bound through a linking biological compound (such as an antibody) which is attached to the support. By preferentially is meant that no other materials bind to the membrane.

Therefore, within about 10 minutes, and preferably within 1 to 5 minutes, of the contact, the bound antigen is contacted with suitable antibody (either directed to a chlamydial or gonococcal antigen) so as to form an immunological complex on the support. If the assay is carried out using a disposable test device, the support can be a microporous membrane through which fluid and uncomplexed materials in the specimen are allowed to flow through as the antigen is bound to the membrane.

The antibodies used in this assay can be polyclonal or monoclonal which can be purchased or prepared using known procedures.

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include tetramethylbenzidine and derivatives thereof, and leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a most preferred embodiment, the chlamydial or gonococcal antibody is not labeled, and detection of the antibody-antigen complex formed and bound to the support is accomplished using a second antibody (described below) which is specific to the unlabeled antibody, respectively, and appropriately labeled.

The antigen-antibody complex can be formed in the presence of one or more proteins which reduce nonspecific interactions on the support. Useful proteins are well known and include, for example, casein, α-casein, fetal bovine serum and porcine gamma globulin. A particularly useful blocking composition comprises a nonimmunological protein and an amphoteric surfactant, as described and claimed in copending and commonly assigned U.S. Ser. No. 255,425 filed on even date herewith by Pronovost and entitled "Immunological Reagent Composition and Its Use in the Determination of Chlamydial or Gonococcal Antigens."

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with a wash solution which generally has a pH of from about 7 to about 11. The solution preferably contains one or more surfactants to aid in separating uncomplexed materials from the complex on the support. Particularly useful surfactants are cationic surfactants. Preferred wash solutions are the subject of copending U.S. Ser. No. 255,924, filed on even date herewith by Pronovost and Gilbert and entitled "Wash Solution Containing a Cationic Surfactant and Its Use in Chlamydial and Gonococcal Assays."

In the embodiment described above where the chlamydial or gonococcal antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures.

In the preferred embodiment, the chlamydial or gonococcal antibody is unlabeled, and after washing the bound complex, it is contacted with an antibody directed to the unlabeled antibody. This second antibody (that is an anti-antibody) is appropriately labeled with any of the labels described above. The antibody can be monoclonal or polyclonal and either purchased or prepared using known techniques.

After this contact, the resulting antigen-antibody-antibody complex which is bound to the support is incubated for up to about 10 minutes at a temperature of from about 15° to about 30° C. Preferably, the incubation is at room temperature for up to about 5 minutes.

Further washing is carried out to removed uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The following examples are provided to illustrate, but not limit the scope of, the present invention.

Amideck TM protease (BioProducts Division, Eastman Kodak Company) used in Example 7 was a subtilisin analog having aspartic acid in amino acid position 76, and serine in both of positions 109 and 218.

Single-stranded DNA from bacteriophage M13mp18 apr4 [Ser$^{109}$, Ser$^{218}$] (from M13mp18 bacteriophage available from Bethesda Research Laboratories, Gaithersburg, Md. catalog no. 8227SA) was annealed to a primer:

```
            *
5' GCT CTT GAT AAC TCA ATC 3'
    74  75  76  77  78  79
    Ala Leu Asp Asn Ser Ile
``` wherein G, C, T, A, are standard symbols for the nucleotide bases, and Ala, Leu, Asp, Asn, Ser and Ile are standard abbreviations for amino acids. This primer was synthesized by the phosphite method described by Beaucage et al, *Tetrahedron Letters* 22, pp. 1859–1862 (1981). It was homologous to the nucleotides comprising codons for amino acids 74 through 79 of aprA-subtilisin except for one base change (marked by the asterisk), where adenine was changed to guanine to allow for the transition which would change Asn$^{76}$ (codon AAT) to Asp$^{76}$ (codon GAT).

The primer was annealed to M13mp18apr4 [Ser$^{109}$, Ser$^{218}$] DNA at 65° C. and the annealed DNA was slowly cooled to approximately 22° C. and then polymerized for two hours at 15° C. in a reaction mixture which consisted of 12.5 μl of annealed DNA solution, 20 μl of 10 mmolar each of dATP, dCTP and dGTP, 20 μl of 12 mmolar ATP, 0.1 μl Klenow DNA polymerase, 0.1 μl T4 DNA ligase and 13 μl sterile distilled water. The resulting double-stranded, covalently closed circular DNA was introduced into *E. coli* JM103 (available from Pharmacia Inc., Piscataway, N.J. catalog no. 27-1545-01) by transfection.

Bacteriophage plaques were transferred to hybridization membranes (such as Gene Screen TM available from New England Nuclear, Beverly, Mass.) and those which contained DNA with the desired base change were identified by hybridization to a radioactively labeled ($\gamma^{32}$P) synthetic oligonucleotide at 46° C. One positive plaque contained a bacteriophage designated as M13mp18 apr4[Asp$^{76}$, Ser$^{109}$, Ser$^{218}$]. Double-stranded DNA from the bacteriophage was digested with HindIII and KpnI in combination, then a 750 bp fragment carrying the three mutations of the aprA-subtilisin gene was ligated to the plasmid pAMB106 which had been previously digested with HindIII and KpnI. The resulting plasmid, pAMB131, was introduced into *B. subtilis* host cells for synthesis and secretion of [Asp$^{76}$, Ser$^{109}$, Ser$^{218}$]-subtilisin (that is protease).

The activity of this protease was determined using the synthetic peptide:

succinyl-L-Ala-L-Ala-L-Pro-L-Phe-p-nitroanilide (available from Sigma Chemical) as a substrate while monitoring the rate of increase in absorbance at 410 nm due to the release of p-nitroaniline. A typical reaction mixture (1 ml) contained tris(hydroxymethyl)aminomethane hydrochloride buffer (0.5 molar, pH 8), calcium chloride (1 mmolar), the peptide noted above (1 mmolar), and the protease activity was measured continuously at 25° C. Specific activity is expressed as units/mg of solid with 1 unit equivalent to a change of absorbance of 1.0 measured at 410 nm within 1 minute.

EXAMPLES 1-3

Improved Stability of Reducing Agent in Aqueous Solutions

These examples illustrate the improved stability provided by mixing a hydrophilic polymer with a sulfhydryl-containing reducing agent to provide aqueous solutions of this invention.

Several keeping tests were performed. The first test was performed at room temperature (18°-25° C.) for 14 days in a aqueous solution. The second and third tests were performed, respectively, at 35° C. for 7 weeks (equivalent to about 39 weeks at room temperature), and at 70° C. for 7 weeks (equivalent to about 79 weeks at room temperature).

An assay for dithiothreitol activity was carried out during the keeping tests using the procedure of Ellman (*Archives of Biochem/Biophysics*, 82, p. 70, 1959) and Ellman's reagent. Optical densities were measured at 412 nm when reagents were first mixed and at various times during the keeping tests. The percentage of dithiothreitol remaining was the calculated from the difference between the optical densities at the beginning of the test and at the end of the keeping period. Ellman's reagent is prepared by dissolving 5,5'-dithiobis(2-nitrobenzoic acid) (39.6 mg) in sodium phosphate buffer (10 ml, 0.1 molar, pH 7.0).

Buffered solutions of reducing agent and hydrophilic polymer were prepared as follows:

EXAMPLE 1

Prepared from 2-(N-morpholino)ethanesulfonic acid (300 μl, 100 mmolar, pH 6.0), sodium azide (300 μl, 1 mg/ml water), ethylenediaminetetraacetic acid (20 mg/ml water), water (372 μl), 5,5-dimethyl-1,3-cyclohexanedione (9 mg in 150 μl ethanol), poly(acrylamide-co-vinylpyrrolidone) (50:50 weight ratio) (18.02% solids) and dithiothreitol (87.5 mg, BioRad Electrophoresis grade). The final polymer concentration was about 10% (by weight).

EXAMPLE 2

Prepared as in Example 1 except that the polymer was poly(acrylamide) (1.6 ml of a 25% solution in water), and a final concentration of 12.7% (by weight).

EXAMPLE 3

Prepared as in Example 2 except the polymer amount was 800 μl of a 25% solution in water, final concentration of 6.35% (by weight).

Stability Tests

Solutions of dithiothreitol were prepared as follows:

A solution of TRIZMA TM (Sigma Chemical Co.) buffer (20 μl, 200 mg/ml water, containing 0.01 weight % thimerosal preservative) was mixed with a solution of 2-(N-morpholino)ethanesulfonic acid (280 μl, 10 mmolar, pH 6.0), sodium chloride (50 mmolar), calcium chloride (5 mmolar), 1,2-propanediol (10% w/v) and preservative (0.01 weight %).

This solution was added to separate test tubes together with each of the solutions of Examples 1-3 above (50 μl), and mixed therein. The resulting mixtures were then diluted 1:100 by adding 100 μl of each solution to 9.9 ml of water. These final solutions were used as "vehicle" solutions.

First portions (90 μl) of the vehicle solutions were added to Ellman's reagent (20 μl) in water (740 μl) and potassium phosphate buffer (200 μl, 0.1 molar, pH 8.0). The optical densities were then recorded for each of Examples 1, 2 and 3.

Second portions (90 μl) of the vehicle solutions were kept at room temperature for 14 days, then added to Ellman's reagent as above. The optical densities were then recorded for each of Examples 1, 2 and 3.

The percentage of dithiothreitol remaining after 14 days was then calculated from the differences in optical densities. The results are shown below.

TABLE I

| Example | Percentage Dithiothreitol Remaining |
|---------|-------------------------------------|
| 1 | 95.9 |
| 2 | 94.2 |
| 3 | 94.3 |

EXAMPLES 4-6

Extraction Blocks Containing Dried Coatings of Reducing Agent and Polymer

Extraction devices like those described in U.S. Pat. No. 4,746,614 (noted above) were prepared and used in these examples. Articles of this invention were prepared by drying coatings of the solutions (50 μl of each) of Examples 1-3, respectively, within the devices at room temperature for about 15 hours. The Example 4 article corresponds to use of the Example 1 solution, and similarly for Examples 5 and 6. A Control device was prepared from a Control solution prepared like in Example 1 except the polymer was omitted. A solution of TRIZMA TM buffer (20 μl of 200 mg/ml solution) containing thimerosal preservative (0.01% by weight) was also placed into the extraction devices in a separate location from the dithiothreitol coatings and allowed to dry for about 15 hours at room temperature.

One group of extraction devices containing dried coatings were treated with a solution (280 μl) containing 2-(N-morpholino)ethanesulfonic acid buffer (10 mmolar, pH 6.0), sodium chloride (50 mmolar), calcium chloride (5 mmolar) 1,2-propanediol (10% w/v) and preservative (0.01% by weight) to dissolve the coated materials. The resulting solutions were then diluted 1:100 by adding them (100 μl) to water (9.9 ml). The diluted solutions (90 μl) were then added to cuvettes containing Ellman's reagent (20 μl) in water (740 μl) and potassium phosphate buffer (200 μl, 0.1 molar, pH 8.0). The optical densities were recorded at 412 nm.

Another group of extraction devices containing dried coatings were placed in sealed bags containing dessicant and an oxygen scavenger. Some devices were kept at 35° C. for 7 weeks and others were kept at 70° C. for 7 weeks.

After the keeping period, the devices were treated as described above for the first group of devices, that is, treatment with buffered solution and Ellman's reagent, and measurement of optical densities at 412 nm. The percentage of dithiothreitol activity remaining after the keeping periods was calculated. The results are shown in Tables II and III below. It is evident that the presence of the hydrophilic polymer with the sulfhydryl-containing reducing agent increases its keeping stability.

TABLE III

| Example | Percentage Dithiothreitol Remaining (after 7 weeks, 70° C.) |
|---------|-------------------------------------------------------------|
| 4 | 43.1 |
| 5 | 100.0 |
| 6 | 94.5 |
| Control | 13.0* |

*after 3 weeks at 70° C.

TABLE II

| Example | Percentage Dithiothreitol Remaining (after 7 weeks, 35° C.) |
|---------|-------------------------------------------------------------|
| 4 | 51.9 |
| 5 | 92.9 |
| 6 | 81.7 |

EXAMPLE 7

Assay for LPS Antigen Using Stabilized Dithiothreitol and a Protease

This example illustrates the practice of the present invention for the determination of the lipopolysaccharide antigen of chlamydial organisms using the Amideck TM protease, described above, and dithiothreitol stabilized by poly(acrylamide).

Eighteen specimens were obtained from female patients using endocervical swabs. The specimens contained considerable whole blood or mucous or both, and had been tested for the presence of C. trachomatis using standard culture techniques.

Materials Used

An extraction device like that described in U.S. Pat. No. 4,746,614 (noted above) was prepared having separate dried coatings of: (1) tris(hydroxymethyl)aminomethane buffer (from 20 µl of a 1.65 molar solution, pH 11.1) with thimerosal preservative (0.01 weight %), and (2) a mixture of dithiothreitol (0.188 molar) from a 50 µl solution containing 2-(N-morpholino)ethanesulfonic acid buffer (10 mmolar, pH 6.0), sodium azide (1.54 mmolar), ethylenediaminetetraacetic acid (5.4 mmolar) dimedone (21.4 mmolar) and poly(acrylamide)(6.35 weight %).

A protease solution was prepared having Amideck™ protease (4 mg/ml, 170 units/mg), 2-(N-morpholino)ethanesulfonic acid buffer (10 mmolar, pH 6), sodium chloride (50 mmolar), calcium chloride (5 mmolar), 1,2-propanediol (10% w/v) and preservative (0.01 weight %).

A hydrogen peroxide solution was prepared containing 12% (by weight) hydrogen peroxide, diethylenetriaminepentaacetic acid (10 µmolar) and preservative (0.01 weight %).

The wash solution contained 3-cyclohexylamino-2-hydroxy-1-propanesulfonic acid buffer (pH 10.0, 0.05 molar), Emcol™ CC-9 cationic surfactant (0.75 weight %) and preservative (0.01 weight %).

A Control reagent solution comprised anti-creatine kinase-MB antibodies (5 µg/ml), casein (0.5 weight %), Lonzaine™ C amphoteric surfactant (0.01 weight %), preservative (0.01 weight %) in phosphate buffered saline solution (pH 7.2).

Monoclonal antibodies to the lipopolysaccharide antigen (4 µg/ml) were supplied in phosphate buffered saline solution (pH 7.2) also containing casein, Lonzaine™ C amphoteric surfactant and preservative as noted above.

Goat anti-mouse IgG antibodies conjugated to horseradish peroxidase (conjugate available from Bio-Rad) (1:700 dilution) were supplied in phosphate buffered saline solution (pH 7.2) with casein, Lonzaine™ amphoteric surfactant and preservative as noted above as well as 4'-hydroxyacetanilide (10 mmolar).

A leuco dye composition contained 2-(4-hydroxy-3-methoxyphenyl)-4,5-bis(4-methoxyphenyl)imidazole leuco dye (0.008 weight %), poly(vinylpyrrolidone) (1 weight %), sodium phosphate buffer (pH 6.8, 10 mmolar), diethylenetriaminepentaacetic acid (10 µmolar), 4'-hydroxyacetanilide (2 mmolar) and hydrogen peroxide (10 mmolar).

Assay

The assay was performed as follows for each of the eighteen specimens obtained using a separate test device for each specimen. The protease solution (about 280 µl) was added to the extraction device and a patient swab was then placed therein, rotated for 5–10 seconds, followed by incubation for 3 minutes at room temperature (that is, 18°–25° C.).

The extraction solution (about 280 µl) was then added to the device containing the swab which was then rotated for another 5–10 seconds followed by incubation at room temperature for 3 minutes.

The hydrogen peroxide solution was added to the device and the same procedure was repeated.

The resulting solution in the extraction device was then removed from the device using a pipette, prefiltered and transferred to each well of a disposable test device like those described in U.S. Ser. No. 19,810 (described above), adding about 160 µl to each well. One well (#1) of each test device was considered a Control well while two others (#2 and #3) were considered test wells. The vent in the device was opened allowing drainage of all fluids. Each well was then washed with the wash solution described above (160 µl) with drainage.

The Control antibody solution (about 80 µl) was added to well #1 while the antilipopolysaccharide antibody solution (about 80 µl) was added to each of wells #2 and #3 without drainage. Incubation at room temperature was carried out for 2 minutes.

After drainage, the wash step was repeated, and the peroxidase-labeled antibody solution (about 80 µl) was added to all wells without drainage, followed by incubation at room temperature for 5 minutes.

Following drainage and another wash step, the leuco dye composition was added to each well without drainage. After incubation at room temperature for 5 minutes, dye formation was stopped by the addition of 0.01% sodium azide solution (about 120 µl) to each well. The dye formed on the membrane of each well was observed visually and graded (0 to 10, with 0 representing no color). The results are provided in the following Table IV and compare the assay results to those found with the standard culture techniques. It can be seen that the assay was highly accurate, determining all negative specimens and 83% of the positive specimens.

TABLE IV

| Specimen | Culture Results | Visual Readings | | | Assay +/− |
|---|---|---|---|---|---|
| | | Control | Well #2 | Well #3 | |
| 1 | Positive | 2–3 | 4 | 4 | Positive |
| 2 | Negative | 1–2 | 1–2 | 1–2 | Negative |
| 3 | Negative | 2 | 2 | 2 | Negative |
| 4 | Negative | 1 | 1 | 0–1 | Negative |
| 5 | Positive | 1 | 10 | 10 | Positive |
| 6 | Negative | 1–2 | 0–1 | 0–1 | Negative |
| 7 | Positive | 1 | 10 | 10 | Positive |
| 8 | Negative | 2–3 | 2 | 2 | Negative |
| 9 | Positive | 1 | 6 | 6 | Positive |
| 10 | Positive | 1–2 | 5 | 5 | Positive |
| 11 | Positive | 1–2 | 1 | 1 | Negative |
| 12 | Positive | 6 | 7 | 7 | * |
| 13 | Positive | 1 | 5–6 | 5–6 | Positive |
| 14 | Positive | 1 | 7–8 | 7–8 | Positive |
| 15 | Positive | 1 | 10 | 10 | Positive |
| 16 | Positive | 1 | 9 | 9 | Positive |
| 17 | Positive | 1 | 5–6 | 5–6 | Positive |
| 18 | Positive | 1 | 1 | 0–1 | Negative |

*No test, that is, assay procedure was done incorrectly.

The invention has been described in detail with particular reference to preferred embodiments thereof, but it will be understood that variations and modifications can be effected within the spirit and scope of the invention.

I claim:

1. An extraction composition useful for the extraction of chlamydial or gonococcal antigen from chlamydial or gonococcal organisms, respectively, comprising:
   one or more reagents useful for extracting chlamydial or gonococcal antigens, respectively, said reagent being selected from the group consisting of surfactants, enzymes and bile salts,
   a sulfhydryl-containing reducing agent which is a thiol, and
   one or more hydrophilic polymers present in an amount effective to stabilize said reducing agent, said hydrophilic polymer selected from the group consisting of vinylpyrrolidone polymers, acrylamide and methacrylamide polymers, acrylic and methacrylic acid polymers, polyethylene glycols and polyamines.

2. The extraction composition of claim 1 wherein said composition further comprises an alcoholamine or salt thereof.

3. The extraction composition of claim 1 which includes ethanolamine or a salt thereof, and wherein said reducing agent is dithiothreitol and said hydrophilic polymer is poly(acrylamide).

4. A diagnostic test kit useful for the determination of chlamydial or gonococcal antigens comprising, separately packaged:
   (a) an extraction solution comprising one or more reagents useful for the extraction of chlamydial or gonococcal antigens from chlamydial or gonococcal organisms, respectively, said reagent being selected from the group consisting of surfactants, enzymes and bile salts, and
   (b) an aqueous composition comprising a sulfhydryl-containing reducing agent which is a thiol, and one or more hydrophilic polymers present in an amount effective to stabilize said reducing agent, said hydrophilic polymer selected from the group consisting of vinylpyrrolidone polymers, acrylamide and methacrylamide polymers, acrylic and methacrylic acid polymers, polyethylene glycols and polyamines.

5. The kit of claim 4 further comprising:
an extraction device for extracting said antigens from chlamydial or gonococcal organisms, respectively, in a biological specimen,
a disposable test device containing a microporous membrane in which said determination can be made,
one or more immunological reagent compositions containing antibodies, one of which antibodies being directed to said extracted antigens, and the same or a different antibody being labeled for detection, and
provided when said labeled antibody comprises an enzyme label, said kit further comprises a composition for providing a detectable species in response to enzymatic activity of said enzyme label.

6. A diagnostic test kit useful for the determination of chlamydial or gonococcal antigens, comprising, separately parkaged:
   (a) an extraction solution comprising one or more reagents useful for extracting chlamydial or gonococcal antigens from chlamydial or gonococcal organisms, respectively, said reagent being selected from the group consisting of surfactants, enzymes and bile salts, and
   (b) an article comprising a water-insoluble substrate having thereon a dried coating of a sulfhydryl-containing reducing agent which is a thiol, in admixture with one or more hydrophilic polymers, said hydrophilic polymer being present in an amount effective to stabilize said reducing agent and being selected from the group consisting of vinylpyrrolidone polymers, acrylamide and methacrylamide polymers, acrylic and methacrylic acid polymers, polyethylene glycols and polyamines.

7. The test kit of claim 6 wherein the ratio of said polymer to said reducing agent in said dried coating is at least about 1:10.

8. A method for extracting antigen from chlamydial or gonococcal organisms comprising:
   A. providing a specimen suspected of containing chlamydial or gonococcal organisms, and
   B. extracting a chlamydial or gonococcal antigen from said organisms, respectively, by contacting the specimen with an extraction composition comprising:
      one or more reagents useful for extraction of said antigen, said reagent being selected from the group consisting of surfactants, enzymes and bile salts,
      a sulfhydryl-containing reducing agent which is a thiol, and
      one or more hydrophilic polymers present in an amount effective to stabilize said reducing agent, said hydrophilic polymer being selected from the group consisting of vinylpyrrolidone polymers, acrylamide and methacrylamide polymers, acrylic and methacrylic acid polymers, polyethylene glycols and polyamines.

9. The method of claim 8 wherein said specimen contains chlamydial organisms, and the lipopolysaccharide antigen of said organisms is extracted with said extraction composition, and said extraction composition further comprises an alcoholamine or salt thereof.

10. A method for the determination of a chlamydial or goncoccal antigen comprising:
    A. extracting chlamydial or gonococcal antigen from a specimen suspected of containing chlamydial or gonococcal organisms, respectively, with an extraction composition comprising:
       one or more reagents useful for extracting said antigens, said reagent being selected from the group consisting of surfactants, enzymes and bile salts,
       a sulfhydryl-containing reducing agent which is a thiol, and
       one or more hydrophilic polymers present in an amount effective to stabilize said reducing agent, said hydrophilic polymer being selected from the group consisting of vinylpyrrolidone polymers, acrylamide and methacrylamide polymers, acrylic and methacrylic acid polymers, polyethylene glycols and polyamines.

11. The method of claim 10 for the determination of the lipopolysaccharide antigen from chlamydial organisms.

12. The method of claim 10 wherein said antibodies to said antigen are labeled, and the presence of said complex is determined by detecting said label in said complex.

13. The method of claim 10 wherein said antibodies to said antigen are unlabeled, said complex is reacted with labeled antibodies directed to said unlabeled antibodies, and determination is accomplished by detecting the resulting antigen-antibody-antibody complex.

14. The method of claim 10 wherein said extraction composition further comprises an alcoholamine or a salt thereof.

15. The method of claim 10 wherein the ratio of said polymer to said reducing agent is at least about 1:10.

16. The extraction composition of claim 11 wherein said sulfhydryl-containing reducing agent is selected from the group consisting of 1,3-dimercapto-2-propanol, 2,3-dimercapto-1-propanol, 1,2-dimercaptoethane, dithiothreitol, dithioerythritol, mercaptoethanol, thioglycerol, glutathione, N-actylcysteine, cysteine, thioglycolic acid, L-cysteinemethyl ester, L-cysteineethyl ester and N-acetyl-D,L-isocysteine.

* * * * *